(12) United States Patent
Breton et al.

(10) Patent No.: US 6,572,664 B2
(45) Date of Patent: *Jun. 3, 2003

(54) INDOLIZINE DERIVATIVES, COMPOSITIONS COMPRISING AT LEAST ONE COUPLER CHOSEN FROM INDOLIZINE DERIVATIVES AND AT LEAST ONE OXIDATION BASE, AND METHODS FOR USING SAME

(75) Inventors: Philippe Breton, Le Chesnay (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/791,914

(22) Filed: Feb. 26, 2001

(65) Prior Publication Data

US 2002/0170121 A9 Nov. 21, 2002

(30) Foreign Application Priority Data

Feb. 25, 2000 (FR) ............................. 00 02420

(51) Int. Cl.[7] ................................. A61K 7/13
(52) U.S. Cl. ................ 8/405; 8/405; 8/409; 8/410; 8/423; 424/62; 424/489; 546/112
(58) Field of Search .............. 8/10.2, 11, 405, 8/409, 410, 423; 424/62, 489; 221/1; 260/296, 293.53; 546/112

(56) References Cited

U.S. PATENT DOCUMENTS

| | | | | |
|---|---|---|---|---|
| 3,642,807 A | * | 2/1972 | Walter et al. | 260/296 |
| 3,717,644 A | * | 2/1973 | Walter et al. | 260/293.53 |
| 4,003,699 A | | 1/1977 | Rose et al. | 8/10.2 |
| 4,013,404 A | | 3/1977 | Parent et al. | 8/11 |
| 4,168,953 A | | 9/1979 | Rose | 8/10.2 |
| 4,823,985 A | | 4/1989 | Grollier et al. | 222/1 |
| 5,061,289 A | | 10/1991 | Clausen et al. | 8/405 |
| 5,380,340 A | | 1/1995 | Neunhoeffer et al. | 8/405 |
| 5,766,576 A | | 6/1998 | Löwe et al. | 424/62 |
| 5,980,585 A | | 11/1999 | Terranova et al. | 8/409 |
| 6,099,593 A | | 8/2000 | Terranova et al. | 8/409 |
| 6,284,277 B1 | * | 9/2001 | Bouloumie et al. | 424/489 |

FOREIGN PATENT DOCUMENTS

| | | |
|---|---|---|
| DE | 1 492 166 | 12/1969 |
| DE | 23 59 399 | 6/1975 |
| DE | 26 23 564 | 12/1977 |
| DE | 38 43 892 | 6/1990 |
| DE | 41 33 957 | 4/1993 |
| DE | 195 43 988 | 5/1997 |
| FR | 2 586 913 | 3/1987 |
| FR | 2 733 749 | 11/1996 |
| FR | 2 746 307 | 9/1997 |
| FR | 2 750 048 | 12/1997 |
| FR | 2 772 267 | 6/1999 |
| GB | 1 026 978 | 4/1966 |
| GB | 1 153 196 | 5/1969 |
| JP | 2-19576 | 1/1990 |
| JP | 03-113847 | * 5/1991 |
| JP | 03-164292 | * 7/1991 |
| JP | 9-110659 | 4/1997 |
| WO | WO 94/08969 | 4/1994 |
| WO | WO 94/08970 | 4/1994 |
| WO | WO 96/15765 | 5/1996 |

OTHER PUBLICATIONS

Co–pending Application—Attorney Docket No. 05725.0858–00000, Compositions for Dyeing Keratin Fibres, Containing Cationic Indolizine Derivatives, and Dyeing Process, Philippe Breton et al., filing date Feb. 26, 2001.

Thomas Peglow et al., "Electrochemically Induced Hetero–[4+2]–Cycloaddition Reactions Between 2–Vinylpyrroles and β–Acceptro–Substituted Enamines", Chemistry—A European Journal, vol. 4, No. 1, 1998, pp. 107–112.

Chemical Abstracts, vol. 91, No. 15, Oct. 1979, Abstract No. 123619v.

English language Derwent Abstract of DE 1 492 166. Dec. 11, 1969.

English language Derwent Abstract of FR 2 733 749, Nov. 8, 1996

English language Derwent Abstract of FR 2 746 307, Dec. 26, 1997.

English language Derwent Abstract of JP 2–10576, Jan. 23, 1990.

English language Derwent Abstract of JP 9–110659.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

Compositions for oxidation dyeing of keratin fibers comprising at least one oxidation base and at least one coupler chosen from indolizine derivatives, methods for using the same for oxidation dyeing of keratin fibers, and compounds chosen from indolizine derivatives.

63 Claims, No Drawings

INDOLIZINE DERIVATIVES, COMPOSITIONS COMPRISING AT LEAST ONE COUPLER CHOSEN FROM INDOLIZINE DERIVATIVES AND AT LEAST ONE OXIDATION BASE, AND METHODS FOR USING SAME

The present invention relates to compositions for oxidation dyeing of keratin fibers comprising at least one oxidation base and at least one coupler chosen from specific indolizine derivatives.

Dye compositions comprising oxidation dye precursors are known in the art for dyeing keratinous fibers, such as human hair. The oxidation dye precursors include ortho-phenylenediamines, para-phenylenediamines, ortho-aminophenols, para-aminophenols, and heterocyclic compounds. These are generally known as oxidation bases. The oxidation dye precursors, or oxidation bases, are generally colorless or weakly colored compounds which may give rise to colored compounds and dyes when combined with oxidizing products via oxidative coupling.

The shades obtained with these oxidation bases may be varied by combining them with couplers or coloration modifiers. Such coloration modifiers may, for example, be chosen from aromatic meta-diamines, meta-aminophenols, meta-diphenols, and certain heterocyclic compounds, such as indole compounds. The variety of oxidation bases and couplers may allow a rich palette of colors to be obtained.

The so-called "permanent" coloration obtained from using these oxidation dyes should have at least one of the following desirable characteristics. The coloration should have no toxicological drawbacks, the shades obtained should have the desired intensity, and the coloration should have good resistance to external agents to which the fibers may be subjected, such as light, bad weather, washing, permanent-waving, perspiration, and rubbing. The dyes should allow coverage of white hairs, and should be as unselective as possible, that is, they should allow only the the smallest possible differences in coloration along the same keratin fiber, which may be differently sensitized (i.e. damaged) between its end tip and its root.

Indazole-type compounds have been used in the field of hair dyeing. For example, in DE-A-1 492 166, the disclosure of which is incorporated herein by reference, the polycondensation of such compounds via oxidation has been proposed, in DE-A-2 623 564, the disclosure of which is incorporated herein by reference, it has been proposed to combine hydroxy-indazoles with tetraaminopyrimidines, and in U.S. Pat. No. 4 013 404, the disclosure of which is incorporated herein by reference, certain aminoindazoles and their use as oxidation dye precursors have been proposed.

The inventors have discovered that it may be possible, by using specific indolizine derivatives, to obtain novel dyes which are at least one of the following: powerful, unselective, resistant, and capable of generating intense colorations in varied shades.

Specifically, one subject of the present invention is a composition for oxidation dyeing of keratin fibers comprising, in a medium suitable for oxidation dyeing:
  (i) at least one oxidation base; and
  (ii) at least one coupler chosen from indolizine derivatives of formula (I) and the acid addition salts thereof:

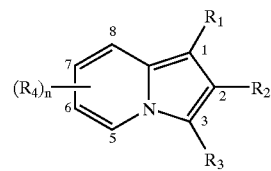

wherein:
  n is an integer ranging from 0 to 4;
  $R_1$ and $R_3$, which may be identical or different, are each chosen from a hydrogen atom; halogen atoms; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino($C_1$–$C_4$)alkyl radicals; ($C_1$–$C_4$)alkoxy($C_1$–$C_4$)alkyl radicals; mono($C_1$–$C_4$)alkylamino ($C_1$–$C_4$)alkyl radicals; di($C_1$–$C_4$)alkylamino($C_1$–$C_4$) alkyl radicals; aminocarboxy($C_1$–$C_4$)alkyl radicals; acetyl($C_1$–$C_4$)alkylamino($C_1$–$C_4$)alkyl radicals; and aromatic rings, optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals;
  wherein $R_3$ may optionally further be chosen from 5- and 6-membered unsaturated heterocycles; and
  with the proviso that at least one of $R_1$ and $R_3$ is a hydrogen atom;
  $R_2$ and $R_4$, which may be identical or different, are each chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono($C_1$–$C_4$)alkylamino($C_1$–$C_4$)alkyl radicals, di($C_1$–$C_4$)alkylamino($C_1$–$C_4$)alkyl radicals, carboxyl radicals, cyano radicals, carboxy($C_1$–$C_4$)alkyl radicals, nitro radicals, and 5- and 6-membered aromatic rings, optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals.;

As used herein, "at least one" means one or more and thus includes individual components as well as mixtures/combinations. Further, as used herein, unless otherwise noted, alkyl radicals may be chosen from substituted, unsubstituted, linear, branched, and cyclic alkyl radicals. Similarly, as used herein and unless otherwise noted, the alkyl radicals of alkoxy radicals may be chosen from substituted, unsubstituted, linear, branched, and cyclic alkyl radicals.

Non-limiting examples of 6-membered aromatic rings of formula (I) include phenyl rings, nitrophenyl rings, alkylphenyl rings, alkoxyphenyl rings, polyalkyl-phenyl rings and polyalkoxyphenyl rings.

Non-limiting examples of unsaturated 5- and 6-membered heterocycles include pyrrole rings, pyridine rings, pyrimidine rings, imidazole rings, pyrazole rings, oxazole rings, thiazole rings, triazole rings, pyrazolotriazole rings, pyrazoloimidazole rings, pyrrolotriazole rings, pyrazolopyrimidine rings, pyrazolopyridine rings, benzimidazole rings, benzoxazole rings, benzothiazole rings, indole rings, indoline rings, indolidine rings, isoindolidine rings, benzotriazoline rings, pyrazine rings, oxazine rings, triazine rings, quinoline rings, tetrahydro-quinoline rings, benzimidazolidine rings and benzopyrimidine rings.

Compounds comprised within those of formula (I) may be known, for example, in the field of photography, and methods of preparing this type of compound may be disclosed in Chichibabin, Ber. 1927, 60, 1607; Borrows et al., J. Chem. Soc., 1946, 1069; and/or T. Uchida et al., *Synthesis,* 1976, 209–236.

Colorations obtained using the inventive dye compositions may possess at least one of the following desirable characteristics: unselectivity, power, ability to enable a variety of shades, and excellent properties of resistance to at least one of atmospheric agents chosen from light and bad weather, perspiration and treatments to which the hair may be subjected (such as shampooing, permanent-waving, etc.).

In one embodiment, indolizine derivatives of formula (I) are chosen from:

indolizine;
2-methyl-1-phenylindolizine;
2,8-dimethylindolizine;
methyl 2-methylindolizine-6-carboxylate;
2,7-dimethylindolizine;
2-methyl-1-(4-nitrophenyl)indolizine;
8-methyl-2-phenylindolizine;
2-methylindolizine;
7-methyl-2-phenylindolizine;
2-phenylindolizine;
7-methyl-2-(3-nitrophenyl)indolizine;
7-methyl-2-(2,5-dimethoxyphenyl)indolizine;
2-(2-pyridyl)indolizine;
2-(4-N,N-dimethylaminophenyl)indolizine;
2-phenyl-3-[2-(4-pyridyl)ethyl]indolizine;
2-phenyl-3-[2-(2-pyridyl)ethyl]indolizine;
2-ethyl-7-methoxyindolizine;
2-ethyl-8-methoxyindolizine;
ethyl 2-butyl-7-indolizinecarboxylate;
1-ethylindolizine;
6,8-dimethylindolizine;
5-ethyl-7-methylindolizine;
N,N-diethyl-2-methyl-1-indolizinethanamine;
N,N-dimethyl-2-methyl-1-indolizinethanamine;
N-ethyl-2-methyl-1-indolizinethanamine;
N-methyl-2-methyl-1-indolizinethanamine;
2-methyl-1-indolizinethanamine;
5,7-dimethylindolizine;
8-cyano-2-methylindolizine;
1-ethyl-2-methylindolizine;
5-indolizineacetic acid;
dihydroindolizine;
1-indolizinealanine;
6-ethyl-1,2-dimethylindolizine;
3-ethylindolizine;
2-ethyl-1-methylindolizine;
N,N-diethyl-2-methyl-3-indolizinethanamine;
N-ethyl-2-methyl-3-indolizinethanamine;
N-ethyl-N-[2-(2-methyl-3-indolizinyl)ethyl]acetamide;
N-[2-(2-methyl-3-indolizinyl)ethyl]acetamide;
N,N,2-trimethyl-3-indolizinethanamine;
N,2-dimethyl-3-indolizinethanamine;
2-methyl-3-indolizinethanamine;
ethyl 7-indolizinecarboxylate;
ethyl 6-indolizinecarboxylate;
N,N-diethyl-2-methyl-3-indolizinepropanamine;
N-ethyl-N-[3-(2-methyl-3-indolizinyl)propyl]acetamide;
N-ethyl-2-methyl-3-indolizinepropanamine;
N-[3-(2-methyl-3-indolizinyl)propyl]acetamide;
N,N,2-trimethyl-3-indolizinepropanamine;
N,2-dimethyl-3-indolizinepropanamine;
2-methyl-3-indolizinepropanamine;
2-methyl-8-nitroindolizine;
2-methyl-6-nitroindolizine;
N,N'-dimethyl-1,2-indolizinethanamine;
methyl 2-methyl-7-indolizinecarboxylate;
ethyl 2-methyl-7-indolizinecarboxylate;
2-methyl-7-indolizinecarboxamide;
N-ethyl-2-indolizinethanamine;
N-methyl-2-indolizinethanamine;
ethyl 2-methyl-8-indolizinecarboxylate;
2-methyl-8-indolizinecarboxylic acid;
2-methyl-6-methoxyindolizine;
2,8-dimethylindolizine;
8-methylindolizine;
N-[(2-methyl-7-indolizinyl)methyl]acetamide;
7-(aminomethyl)-2-methylindolizine;
2-methyl-7-indolizinecarboxamide;
1-β-hydroxyethyl-2-methylindolizine;
6-hydroxymethyl-2-methylindolizine;
ethyl 6-carboxy-2-methylindolizine;
1-hydroxymethylindolizine;
2-aminomethylindolizine;
2-hydroxymethylindolizine;
2,3,7-trimethylindolizine;
2,3,6-trimethylindolizine;
5-methylindolizine;
3,5-dimethylindolizine;
1-methylindolizine;
2-methylindolizine;
7-methylindolizine;
6-methylindolizine;
3-methylindolizine;
6-ethyl-2,3-dimethylindolizine;
6-ethyl-2-methylindolizine;
1,2-dimethylindolizine;
2,7-dimethylindolizine;
2,6-dimethylindolizine;
2,5-dimethylindolizine;
2,3-dimethylindolizine;
2-(3-furanyl)indolizine;
2-(2-thiazolyl)indolizine;
2-(3-thienyl)indolizine;
2-(2-thienyl)indolizine;

5,7-dimethyl-2-phenylindolizine;
2-(3,4-dimethoxyphenyl)indolizine;
5-carboxy-2-phenylindolizine;
4-(7-indolizinyl)benzenesulphonic acid;
4-(2-indolizinyl)benzenesulphonic acid;
3,8-dimethyl-2-phenylindolizine;
3,7-dimethyl-2-phenylindolizine;
3,6-dimethyl-2-phenylindolizine;
3,5-dimethyl-2-phenylindolizine;
7-methyl-8-nitro-2-phenylindolizine;
7-methyl-6-nitro-2-phenylindolizine;
1-β-aminoethyl-2-phenylindolizine;
8-methyl-2-phenylindolizine;
2-(3-methoxyphenyl)indolizine;
6-ethyl-2-phenylindolizine;
2-(2,5-dimethoxyphenyl)-5-methylindolizine;
2-(2,5-dimethoxyphenyl)indolizine;
6-methyl-2-phenylindolizine;
8-carboxy-2-phenylindolizine;
2-(4-γ-hydroxypropylphenyl)indolizine;
2-(4-β-hydroxyethylphenyl)indolizine;
8-nitro-2-phenylindolizine;
6-nitro-2-phenylindolizine;
6-carboxy-2-phenylindolizine;
6-carboxy-2-phenylindolizine;
5-methyl-2-phenylindolizine;
7-methoxy-2-phenylindolizine;
1-[2-(dimethylamino)ethyl]-2-phenylindolizine;
1-[3-(dimethylamino)propyl]-2-phenylindolizine;
1-[(dimethylamino)methyl]-2-phenylindolizine;
2-(4-methoxyphenyl)indolizine;

and the acid addition salts of any of the foregoing.

According to the present invention, the at least one coupler may be present in the composition in an amount generally ranging from 0.0005% to 12% by weight relative to the total weight of the dye composition, such as from 0.005% to 6% by.

The nature of the at least one oxidation base used in the present invention may not be critical. In one embodiment, the at least one oxidation base is chosen from para-phenylenediamines, double bases, para-aminophenols, ortho-aminophenols, heterocyclic oxidation bases, and the acid addition salts of any of the foregoing. As used herein, "double bases" means compounds comprising at least two aromatic entities substituted with at least one radical chosen from amino radicals and hydroxyl radicals.

Non-limiting examples of para-phenylenediamines which can be used as the at least one oxidation base include compounds of formula (II) and the acid addition salts thereof:

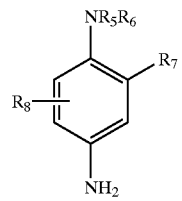

(II)

wherein:

$R_5$ is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$alkyl radicals, $C_1$–$C_4$ alkyl radicals substituted with at least one radical chosen from nitrogen-containing radicals, phenyl radicals and 4'-aminophenyl radicals;

$R_6$ is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$alkyl radicals and $C_1$–$C_4$ alkyl radicals substituted with at least one nitrogen-containing radical;

$R_7$ is chosen from a hydrogen atom, halogen atoms such as a chlorine atom, a bromine atom, an iodine atom and a fluorine atom, $C_1$–$C_4$ alkyl radicals, $C_1$–$C_4$ monohydroxyalkyl radicals, $C_1$–$C_4$ hydroxyalkoxy radicals, acetylamino$(C_1$–$C_4)$alkoxy radicals, mesylamino-$(C_1$–$C_4)$alkoxy radicals and carbamoylamino$(C_1$–$C_4)$ alkoxy radicals;

$R_8$ is chosen from a hydrogen atom, halogen atoms and $C_1$–$C_4$ alkyl radicals.

Non-limiting examples of nitrogen-containing radicals of above formula (II) include amino radicals, mono$(C_1$–$C_4)$ alkylamino radicals, di$(C_1$–$C_4)$alkylamino radicals, tri $(C_1$–$C_4)$alkylamino radicals, monohydroxy$(C_1$–$C_4)$ alkylamino radicals, imidazolinium radicals and ammonium radicals.

Non-limiting examples of para-phenylenediamines of formula (II) include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylamino-ethyloxy-para-phenylenediamine, N-(β-methoxyethyl)-para-phenylenediamine, and the acid addition salts of any of the foregoing.

In one embodiment, para-phenylenediamines of formula (II) are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethylpara-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts of any of the foregoing.

Non-limiting examples of double bases which may be used as the at least one oxidation base according to the present invention include compounds of formula (III) and the acid addition salts thereof:

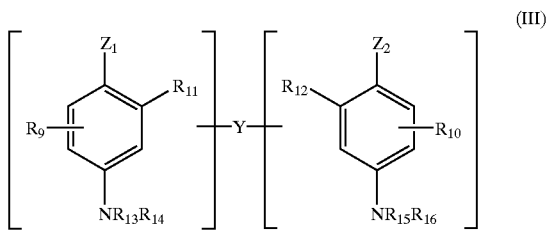

(III)

wherein:
- $Z_1$ and $Z_2$, which may be identical or different, are each chosen from hydroxyl radicals and —$NH_2$ radicals, optionally substituted with at least one radical chosen from $C_1$–$C_4$ alkyl radicals and linker arms Y;
- linker arm Y is chosen from linear and branched divalent alkylene chains comprising from 1 to 14 carbon atoms, wherein said divalent alkylene chains may optionally be interrupted by at least one nitrogen-containing radical and optionally interrupted by at least one heteroatom such as an oxygen atom, a sulphur atom or a nitrogen atom, further wherein said divalent alkylene chains may optionally be terminated with at least one nitrogen-containing radical and optionally interrupted by at least one heteroatom such as an oxygen atom, a sulphur atom or a nitrogen atom, and further wherein said divalent alkylene chains may optionally be substituted with at least one radical chosen from hydroxyl radicals and $C_1$–$C_6$ alkoxy radicals;
- $R_9$ and $R_{10}$, which may be identical or different, are each chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals and linker arms Y;
- $R_{11}$, $R_{12}$, $R_{13}$, $R_{14}$, $R_{15}$ and $R_{16}$, which may be identical or different, are each chosen from a hydrogen atom, linker arms Y and $C_1$–$C_4$ alkyl radicals;

with the proviso that only one linker arm Y is present in each compound of formula (III).

Non-limiting examples of nitrogen-containing radicals of formula (III) include amino radicals, mono($C_1$–$C_4$) alkylamino radicals, di($C_1$–$C_4$)alkylamino radicals, tri ($C_1$–$C_4$)alkylamino radicals, monohydroxy($C_1$–$C_4$) alkylamino radicals, imidazolinium radicals and ammonium radicals.

Non-limiting examples of double bases of formula (III) include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methyl-phenyl)ethylenediamine, 1,8-bis(2,5-diaminophenoxy)-3,5-dioxaoctane, and the acid addition salts of any of the foregoing.

In one embodiment, double bases of formula (III) are chosen from N,N'-bis(β-hydroxyethyl)-N,N'-bis(4'-aminophenyl)-1,3-diaminopropanol, 1,8-bis(2,5-diaminophenoxy)-3,5-dioxaoctane and the acid addition salts of any of the foregoing.

Non-limiting examples of para-aminophenols which may be used according to the present invention include compounds of formula (IV) and the acid addition salts thereof:

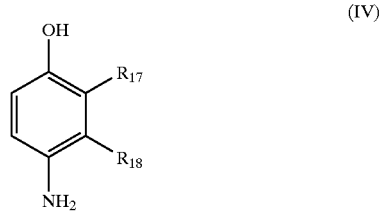

(IV)

wherein:
- $R_{17}$ is chosen from a hydrogen atom, halogen atoms, $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$ aminoalkyl radicals and hydroxy($C_1$–$C_4$)alkylamino ($C_1$–$C_4$)alkyl radicals; and
- $R_{18}$ is chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, cyano($C_1$–$C_4$)alkyl radicals and ($C_1$–$C_4$)alkoxy($C_1$–$C_4$)alkyl radicals, with the proviso that at least one of $R_{17}$ and $R_{18}$ is a hydrogen atom.

Non-limiting examples of para-aminophenols of formula (IV) include of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol and the acid addition salts of any of the foregoing.

Non-limiting examples of ortho-aminophenols which may be used as the at least one oxidation base include 2-aminophenol, 2-amino-5-methylphenol, 2-amino-6-methylphenol, 5-acetamido-2-aminophenol and the acid addition salts of any of the foregoing.

Non-limiting examples of heterocyclic bases which may be used as the at least one oxidation base include pyridine derivatives, pyrimidine derivatives, pyrazole derivatives and the acid addition salts of any of the foregoing.

Non-limiting examples of pyridine derivatives include compounds disclosed, for example, in British Patents GB 1 026 978 and GB 1 153 196, the disclosures of which are incorporated herein by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine and the acid addition salts of any of the foregoing.

Non-limiting examples of pyrimidine derivatives include compounds described, for example, in German Patent DE 2 359 399, Japanese Patents JP 88-169 571 and JP 91-10659, and Patent Application WO 96/15765, the disclosures of which are incorporated herein by reference, such as 2,4,5, 6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in French Patent Application FR-A-2 750 048, the disclosure of which is incorporated herein by reference, such as pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, and the addition salts and tautomeric forms (when there exists a tautomeric equilibrium) of any of the foregoing.

Further non-limiting examples of pyrazole derivatives include compounds described in German Patents DE 3 843 892 and DE 4 133 957 and Patent Applications WO 94/08969, WO 94/08970, FR-A-2 733 749 and DE 195 43 988, the disclosures of which are incorporated hereby by reference, such as 4,5-diamino-1-methylpyrazole, 3,4-diaminopyrazole, 4,5-diamino-l-(4'-chlorobenzyl)pyrazole, 4,5-diamino-1-(β-hydroxyethyl)-pyrazole, 4,5-diamino-1,3-dimethylpyrazole, 4,5-diamino-1-(β-hydroxyethyl) pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methyl pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole and the acid addition salts of any of the foregoing.

According to the present invention, the at least one oxidation base may be present in the composition in an amount generally ranging from 0.0005% to 12% by weight relative to the total weight of the dye composition, such as from 0.005% to 6% by weight.

The dye composition according to the present invention may optionally further comprise at least one additional coupler different from the indolizine derivatives of formula (I) and may optionally further comprise at least one direct dye, for example, to vary and/or enrich the shade obtained using the at least one oxidation base with highlights.

The at least one additional coupler which can be used in the dye composition according to the present invention may be chosen from couplers conventionally used in oxidation dyeing, such as, for example, meta-phenylenediamines, meta-aminophenols, meta-diphenols and heterocyclic couplers such as, for example, indole derivatives, indoline derivatives, benzimidazole derivatives, benzomorpholine derivatives, sesamol derivatives, pyridine derivatives, pyrimidine derivatives, pyrazole derivatives and the acid addition salts thereof.

In one embodiment, the at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one and the addition salts of any of the foregoing.

When present, the at least one additional coupler may be present in the composition in an amount generally ranging from 0.0001% to 10% by weight relative to the total weight of the dye composition, such as from 0.005% to 5% by weight.

According to the present invention, the acid addition salts may be chosen from hydrochlorides, hydrobromides, sulphates, tartrates, lactates and acetates.

The medium suitable for oxidation dyeing, or support, according to the present invention may be chosen from water and a mixture of water and at least one organic solvent in order to dissolve the compounds which might not be sufficiently soluble in water alone. Non-limiting examples of the at least one organic solvent include $C_1$–$C_4$ alkanols such as ethanol and isopropanol; glycerol; glycols and glycol ethers such as 2-butoxyethanol, propylene glycol, propylene glycol monomethyl ether, diethylene glycol, diethylene glycol monomethyl ether; aromatic alcohols such as benzyl alcohol and phenoxyethanol; and analogous solvents.

According to the present invention, the at least one organic solvent maybe present in the composition in an amount generally ranging from 1% to 40% by weight relative to the total weight of the dye composition, such as from 5% to 30% by weight.

The pH of the dye composition in accordance with the present invention generally ranges from 3 to 12. It can be adjusted to the desired value by means of at least one agent commonly used in dyeing keratin fibers chosen from acidifying agents and basifying agents.

Non-limiting examples of acidifying agents include inorganic acids and organic acids such as hydrochloric acid, orthophosphoric acid, carboxylic acids (such as tartaric acid, citric acid and lactic acid) and sulphonic acids.

Non-limiting examples of basifying agents include aqueous ammonia, alkaline carbonates, alkanolamines such as mono-, di- and triethanolamines and derivatives thereof, sodium hydroxide, potassium hydroxide and compounds of formula (V):

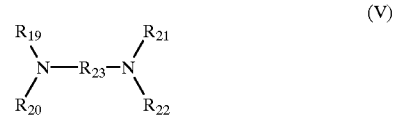

wherein:

$R_{23}$ is chosen from divalent propylene residues, optionally substituted with at least one radical chosen from hydroxyl radicals and $C_1$–$C_4$ alkyl radicals;

$R_{19}$, $R_{20}$, $R_{21}$ and $R_{22}$, which may be identical or different, are each chosen from a hydrogen atom, $C_1$–$C_4$ alkyl radicals and $C_1$–$C_4$ hydroxyalkyl radicals.

According to the present invention, the dye composition may further comprise at least one adjuvant chosen from adjuvants conventionally used in hair dyeing compositions, such as anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, conditioners, such as, for example, silicones, film-forming agents, preserving agents and opacifiers.

Needless to say, a person skilled in the art will take care to choose any optional additional compound(s) such that the advantageous properties associated with the inventive dye compositions are not, or not substantially, adversely affected by the addition(s) envisaged.

According to the present invention, the dye composition may be provided in various forms, such as in the form of a liquid, a cream or a gel, or in any other form suitable for dyeing keratin fibers, such as human hair.

Another subject of the present invention is a process for oxidation dyeing of keratin fibers comprising applying to said keratin fibers for a sufficient time to obtain a desired color at least one dye composition comprising, in a medium suitable for dyeing, (i) at least one coupler chosen from indolizine derivatives of formula (I)and (ii) at least one oxidation base. In one embodiment, the keratin fibers are chosen from human keratin fibers. In another embodiment, the human keratin fibers are hair.

In another embodiment, the at least one dye composition is applied to the keratin fibers, and the desired color may be developed at a pH chosen from acidic, neutral or alkaline pH. Further, the at least one dye composition may further comprise at least one oxidizing agent which may be added to the at least one dye composition at the time of application, and/or which may be present in at least one oxidizing composition. In one embodiment, the at least one oxidizing composition may be applied simultaneously with said at least one dye composition, while in another embodiment, the at least one oxidizing composition may be applied to the keratin fibers sequentially with the at least one dye composition.

In a further embodiment, the at least one dye composition is mixed, at the time of use, with at least one oxidizing composition comprising, in a medium appropriate for dyeing, at least one oxidizing agent present in an amount sufficient to develop a desired coloration. The mixture obtained may subsequently be applied to the keratin fibers and may be left to stand for 3 to 50 minutes, such as for 5 to 30 minutes. In yet another embodiment, the fibers are rinsed, and may optionally be washed with a shampoo, rinsed again and dried.

According to the present invention, the at least one oxidizing agent may be chosen from oxidizing agents conventionally used for the oxidation dyeing of keratin fibers, such as hydrogen peroxide, urea peroxide, alkali metal bromates, persalts such as perborates and persulphates, peracids and enzymes such as peroxidases, laccases, tyrosinases and oxidoreductases (such as pyranose oxidases, glucose oxidases, glycerol oxidases, lactate oxidases, pyruvate oxidases and uricases).

The pH of the at least one oxidizing composition comprising the at least one oxidizing agent after mixing with the at least one dye composition may generally range from 3 to 12, such as from 5 to 11. Further, the pH may be adjusted to a desired value by means of at least one agent chosen from acidifying and basifying agents commonly in dyeing keratin fibers and as defined above.

The at least one oxidizing composition as defined above may also contain at least one adjuvant conventionally used in hair dyeing compositions and as defined above.

The composition which is applied to the keratin fibers may be in various forms, such as in the form of a liquid, a cream or a gel or any other form suitable for carrying out dyeing of keratin fibers, such as human hair.

The present invention also provides a multi-compartment device or kit or any other packaging system, comprising a first compartment containing a first composition comprising at least one dye composition as defined above and a second compartment containing a second composition comprising at least one oxidizing composition as defined above. These devices may be equipped with a means allowing the desired mixture to be deposited on the hair, such as the devices described in French Patent FR-2 586 913, the disclosure of which is incorporated herein.

Finally, this invention provides certain novel indolizine derivatives of formula (I) These novel indolizine derivatives are chosen from methyl 2-methylindolizine-6-carboxylate, 7-methyl-2-(2,5-dimethoxyphenyl)indolizine and the acid addition salts thereof.

According to the present invention, the acid addition salts of these novel compounds may be chosen from those defined above for the compounds of formula (I). These specific compounds may be prepared according to the synthetic processes mentioned above for the compounds of formula (I).

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis.

DYEING EXAMPLES

Examples 1 to 5 of Dyeing in Neutral Medium

The following dye compositions, in accordance with the invention, were prepared:

| EXAMPLE | 1 | 2 | 3 | 4 | 5 |
|---|---|---|---|---|---|
| Methyl 2-methylindolizine-6-carboxylate (coupler of formula (I)) | $3 \times 10^{-3}$ mol | $3 \times 10^{-3}$ mol | $3 \times 10^{-3}$ mol | $3 \times 10^{-3}$ mol | — |
| 2-Methylindolizine (coupler of formula (I)) | — | — | — | — | $3 \times 10^{-3}$ mol |
| para-Phenylenediamine (oxidation base) | $3 \times 10^{-3}$ mol | — | — | — | — |
| para-Tolylenediamine (oxidation base) | — | $3 \times 10^{-3}$ mol | — | — | — |
| 3,7-Diaminopyrazolopyrimidine dihydrochloride (oxidation base) | — | — | $3 \times 10^{-3}$ mol | — | $3 \times 10^{-3}$ mol |
| N-(□-Methoxyethyl)-para-phenylenediamine dihydrochloride (oxidation base) | — | — | — | $3 \times 10^{-3}$ mol | — |
| Common dye support No. 1 | (*) | (*) | (*) | (*) | (*) |
| Demineralized water qs | 100 g | 100 g | 100 g | 100 g | 100 g |

(*): Common dye support No. 1:

| | |
|---|---|
| Ethanol | 18 g |
| Phosphate buffer (1.5M $K_2HPO_4$/1M $KH_2PO_4$) | 10 g |
| Sodium metabisulphite | 0.205 g |
| Sequestering agent | qs |

At the time of use, each of the above dye compositions was mixed weight for weight with a 20-volumes hydrogen peroxide solution (6% by weight) of pH 3.

Each mixture obtained had a pH of approximately 6.8, and was applied for 30 minutes to locks of natural grey hair containing 90% white hairs. The locks were then rinsed, washed with shampoo, rinsed again and then dried.

The shades obtained are given in the table below:

| Example | Shade obtained |
|---|---|
| 1 | very dark grey |
| 2 | dark green |
| 3 | violet |
| 4 | dark green-blue |
| 5 | ash-violet dark blond |

Example 6 of Dyeing in Alkaline Medium

The dye composition below, in accordance with the invention, was prepared:

| EXAMPLE | 6 |
|---|---|
| 2-Methylindolizine (coupler of formula (I)) | $3 \times 10^{-3}$ mol |
| 3,7-Diaminopyrazolopyrimidine dihydrochloride (oxidation base) | $3 \times 10^{-3}$ mol |
| Common dye support No. 2 | (**) |
| Demineralized water qs | 100 g |

(**): Common dye support No. 2:

| | |
|---|---|
| Ethanol | 18 g |
| Aqueous ammonia containing 20% $NH_3$ | 10 g |
| Sodium metabisulphite | 0.205 g |
| Sequestering agent | qs |

At the time of use, the above dye composition was mixed weight for weight with a 20-volume hydrogen peroxide solution (6% by weight) of pH 3.

The mixture obtained had a pH of approximately 10, and was applied for 30 minutes to locks of natural grey hair containing 90% white hairs. The locks were then rinsed, washed with shampoo, rinsed again and then dried.

The hair was dyed in an iridescent ash blond shade.

What is claimed is:

1. A composition for oxidation dyeing of keratin fibers comprising, in a medium appropriate for dyeing keratin fibers:
   (i) at least one oxidation base; and
   (ii) at least one coupler chosen from indolizine derivatives of formula (I) and the acid addition salts thereof:

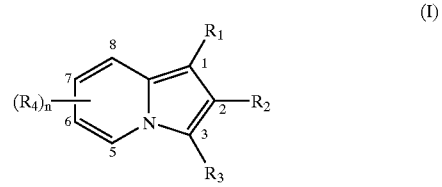

(I)

wherein:

n is an integer ranging from 0 to 4;

$R_1$ and $R_3$, which may be identical or different, are each chosen from a hydrogen atom; halogen atoms; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino($C_1$–$C_4$)alkyl radicals; ($C_1$–$C_4$)alkoxy($C_1$–$C_4$)alkyl radicals; mono($C_1$–$C_4$)alkylamino($C_1$–$C_4$)alkyl radicals; di($C_1$–$C_4$)alkylamino($C_1$–$C_4$)alkyl radicals; aminocarboxy($C_1$–$C_4$)alkyl radicals; acetyl($C_1$–$C_4$)alkylamino($C_1$–$C_4$)alkyl radicals; and aromatic rings, optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals;

wherein $R_3$ may optionally further be chosen from 5- and 6-membered unsaturated heterocycles; and with the proviso that at least one of $R_1$ and $R_3$ is a hydrogen atom;

$R_2$ and $R_4$, which may be identical or different, are each chosen from a hydrogen atom, halogen atoms, C₁–C₄ alkyl radicals, C₁–C₄ monohydroxyalkyl radicals, C₂–C₄ polyhydroxyalkyl radicals, C₁–C₄ aminoalkyl radicals, mono(C₁–C₄)alkylamino(C₁–C₄)alkyl radicals, di(C₁–C₄)alkylamino(C₁–C₄) alkyl radicals, carboxyl radicals, cyano radicals, carboxy(C₁–C₄)alkyl radicals, nitro radicals, and 5- and 6-membered aromatic rings, optionally substituted with at least one radical chosen from halogen atoms, C₁–C₄ alkyl radicals, trifluoromethyl radicals, C₁–C₄ alkoxy radicals, amino radicals and mono- and disubstituted amino radicals wherein the substituent is chosen from C₁–C₄ alkyl radicals, (C₁–C₄)alkylamino(C₁–C₄)alkyl radicals, di(C₁–C₄) alkylamino(C₁–C₄)alkyl radicals, carboxyl radicals and sulphoxy radicals.

2. A composition according to claim 1, wherein said keratin fibers are human keratin fibers.

3. A composition according to claim 2, wherein said human keratin fibers are hair.

4. A composition according to claim 1, wherein said aromatic rings of formula (I) are chosen from phenyl rings, nitrophenyl rings, alkylphenyl rings, alkoxyphenyl rings, polyalkylphenyl rings and polyalkoxyphenyl rings.

5. A composition according to claim 1, wherein said unsaturated 5- or 6-membered heterocycles are chosen from pyrrole rings, pyridine rings, pyrimidine rings, imidazole rings, pyrazole rings, oxazole rings, thiazole rings, triazole rings, pyrazolotriazole rings, pyrazoloimidazole rings, pyrrolotriazole rings, pyrazolopyrimidine rings, pyrazolopyridine rings, benzimidazole rings, benzoxazole rings, benzothiazole rings, indole rings, indoline rings, indolidine rings, isoindolidine rings, benzotriazoline rings, pyrazine rings, oxazine rings, triazine rings, quinoline rings, tetrahydroquinoline rings, benzimidazolidine rings and benzopyrimidine rings.

6. A composition according to claim 1 wherein said indolizine derivatives of formula (I) are chosen from:
indolizine;
2-methyl-1-phenylindolizine;
2,8-dimethylindolizine;
methyl 2-methylindolizine-6-carboxylate;
2,7-dimethylindolizine;
2-methyl-1-(4-nitrophenyl)indolizine;
8-methyl-2-phenylindolizine;
2-methylindolizine;
7-methyl-2-phenylindolizine;
2-phenylindolizine;
7-methyl-2-(3-nitrophenyl)indolizine;
7-methyl-2-(2,5-dimethoxyphenyl)indolizine;
2-(2-pyridyl)indolizine;
2-(4-N,N-dimethylaminophenyl)indolizine;
2-phenyl-3-[2-(4-pyridyl)ethyl]indolizine;
2-phenyl-3-[2-(2-pyridyl)ethyl]indolizine;
2-ethyl-7-methoxyindolizine;
2-ethyl-8-methoxyindolizine;
ethyl 2-butyl-7-indolizinecarboxylate;
1-ethylindolizine;
6,8-dimethylindolizine;
5-ethyl-7-methylindolizine;
N,N-diethyl-2-methyl-1-indolizinethanamine;
N,N-dimethyl-2-methyl-1-indolizinethanamine;
N-ethyl-2-methyl-1-indolizinethanamine;
N-methyl-2-methyl-1-indolizinethanamine;
2-methyl-1-indolizinethanamine;
5,7-dimethylindolizine;
8-cyano-2-methylindolizine;
1-ethyl-2-methylindolizine;
5-indolizineacetic acid;
dihydroindolizine;
1-indolizinealanine;
6-ethyl-1,2-dimethylindolizine;
3-ethylindolizine;
2-ethyl-1-methylindolizine;
N,N-diethyl-2-methyl-3-indolizinethanamine;
N-ethyl-2-methyl-3-indolizinethanamine;
N-ethyl-N-[2-(2-methyl-3-indolizinyl)ethyl]acetamide;
N-[2-(2-methyl-3-indolizinyl)ethyl]acetamide;
N,N,2-trimethyl-3-indolizinethanamine;
N,2-dimethyl-3-indolizinethanamine;
2-methyl-3-indolizinethanamine;
ethyl 7-indolizinecarboxylate;
ethyl 6-indolizinecarboxylate;
N,N-diethyl-2-methyl-3-indolizinepropanamine;
N-ethyl-N-[3-(2-methyl-3-indolizinyl)propyl]acetamide;
N-ethyl-2-methyl-3-indolizinepropanamine;
N-[3-(2-methyl-3-indolizinyl)propyl]acetamide;
N,N,2-trimethyl-3-indolizinepropanamine;
N,2-dimethyl-3-indolizinepropanamine;
2-methyl-3-indolizinepropanamine;
2-methyl-8-nitroindolizine;
2-methyl-6-nitroindolizine;
N,N'-dimethyl-1,2-indolizinethanamine;
methyl 2-methyl-7-indolizinecarboxylate;
ethyl 2-methyl-7-indolizinecarboxylate;
2-methyl-7-indolizinecarboxamide;
N-ethyl-2-indolizinethanamine;
N-methyl-2-indolizinethanamine;
ethyl 2-methyl-8-indolizinecarboxylate;
2-methyl-8-indolizinecarboxylic acid;
2-methyl-6-methoxyindolizine;
2,8-dimethylindolizine;
8-methylindolizine;
N-[(2-methyl-7-indolizinyl)methyl]acetamide;
7-(aminomethyl)-2-methylindolizine;
2-methyl-7-indolizinecarboxamide;
1-β-hydroxyethyl-2-methylindolizine;
6-hydroxymethyl-2-methylindolizine;
ethyl 6-carboxy-2-methylindolizine;
1-hydroxymethylindolizine;
2-aminomethylindolizine;
2-hydroxymethylindolizine;
2,3,7-trimethylindolizine;
2,3,6-trimethylindolizine;
5-methylindolizine;
3,5-dimethylindolizine;
1-methylindolizine;
2-methylindolizine;
7-methylindolizine;

6-methylindolizine;
3-methylindolizine;
6-ethyl-2,3-dimethylindolizine;
6-ethyl-2-methylindolizine;
1,2-dimethylindolizine;
2,7-dimethylindolizine;
2,6-dimethylindolizine;
2,5-dimethylindolizine;
2,3-dimethylindolizine;
2-(3-furanyl)indolizine;
2-(2-thiazolyl)indolizine;
2-(3-thienyl)indolizine;
2-(2-thienyl)indolizine;
5,7-dimethyl-2-phenylindolizine;
2-(3,4-dimethoxyphenyl)indolizine;
5-carboxy-2-phenylindolizine;
4-(7-indolizinyl)benzenesulphonic acid;
4-(2-indolizinyl)benzenesulphonic acid;
3,8-dimethyl-2-phenylindolizine;
3,7-dimethyl-2-phenylindolizine;
3,6-dimethyl-2-phenylindolizine;
3,5-dimethyl-2-phenylindolizine;
7-methyl-8-nitro-2-phenylindolizine;
7-methyl-6-nitro-2-phenylindolizine;
1-β-aminoethyl-2-phenylindolizine;
8-methyl-2-phenylindolizine;
2-(3-methoxyphenyl)indolizine;
6-ethyl-2-phenylindolizine;
2-(2,5-dimethoxyphenyl)-5-methylindolizine;
2-(2,5-dimethoxyphenyl)indolizine;
6-methyl-2-phenylindolizine;
8-carboxy-2-phenylindolizine;
2-(4-γ-hydroxypropylphenyl)indolizine;
2-(4-β-hydroxyethylphenyl)indolizine;
8-nitro-2-phenylindolizine;
6-nitro-2-phenylindolizine;
6-carboxy-2-phenylindolizine;
6-carboxy-2-phenylindolizine;
5-methyl-2-phenylindolizine;
7-methoxy-2-phenylindolizine;
1-[2-(dimethylamino)ethyl]-2-phenylindolizine;
1-[3-(dimethylamino)propyl]-2-phenylindolizine;
1-[(dimethylamino)methyl]-2-phenylindolizine;
2-(4-methoxyphenyl)indolizine;
and the acid addition salts of any of the foregoing.

7. A composition according to claim 1, wherein said at least one coupler is present in an amount ranging from 0.0005% to 12% by weight relative to the total weight of said composition.

8. A composition according to claim 7, wherein said at least one coupler is present in an amount ranging from 0.005% to 6% by weight relative to the total weight of said composition.

9. A composition according to claim 1, wherein said at least one oxidation base is chosen from para-phenylenediamines, double bases, para-aminophenols, ortho-aminophenols and heterocyclic oxidation bases, and the acid addition salts of the foregoing.

10. A composition according to claim 9, wherein said para-phenylenediamines are chosen from compounds of formula (II) and the acid addition salts thereof:

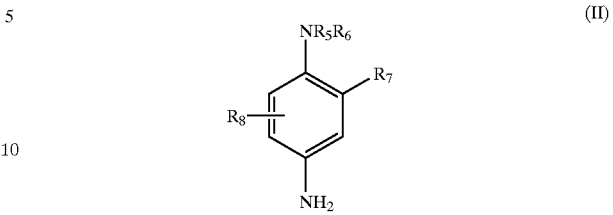

wherein:
$R_5$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, $C_1$–$C_4$ alkyl radicals substituted with at least one radical chosen from nitrogen-containing radicals, phenyl radicals and 4'-aminophenyl radicals;
$R_6$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals and $C_1$–$C_4$ alkyl radicals substituted with at least one nitrogen-containing radical;
$R_7$ is chosen from a hydrogen atom, halogen atoms, $C_1$–$C_4$ alkyl radicals, $C_1$–$C_4$ monohydroxyalkyl radicals, $C_1$–$C_4$ hydroxyalkoxy radicals, acetylamino($C_1$–$C_4$)alkoxy radicals, mesylamino($C_1$–$C_4$)alkoxy radicals and carbamoylamino($C_1$–$C_4$)alkoxy radicals;
$R_8$ is chosen from a hydrogen atom, halogen atoms and $C_1$–$C_4$ alkyl radicals.

11. A composition according to claim 10, wherein said halogen atoms are chosen from chlorine atoms, bromine atoms, iodine atoms and a fluorine atoms.

12. A composition according to claim 10, wherein said nitrogen-containing radicals are chosen from amino radicals, mono($C_1$–$C_4$)alkylamino radicals, di($C_1$–$C_4$)alkylamino radicals, tri($C_1$–$C_4$)alkylamino radicals, monohydroxy ($C_1$–$C_4$)alkylamino radicals, imidazolinium radicals and ammonium radicals.

13. A composition according to claim 10, wherein said para-phenylenediamines of formula (II) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and the acid addition salts of any of the foregoing.

14. A composition according to claim 13, wherein said para-phenylenediamines are chosen from para-phenylenediamine, para-tolylenediamine, 2-iso-propylpara-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts of any of the foregoing.

15. A composition according to claim 9, wherein said double bases are chosen from compounds of formula (III) and the acid addition salts thereof:

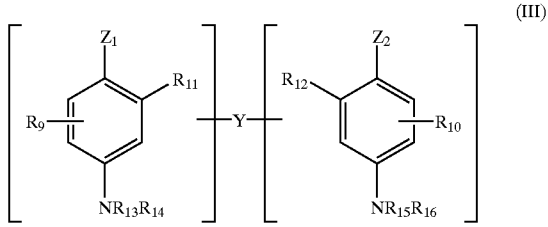

(III)

wherein:
- $Z_1$ and $Z_2$, which may be identical or different, are each chosen from hydroxyl radicals and —$NH_2$ radicals, optionally substituted with at least one radical chosen from $C_1$–$C_4$ alkyl radicals and linker arms Y;
- linker arm Y is chosen from linear and branched divalent alkylene chains comprising from 1 to 14 carbon atoms, wherein said divalent alkylene chains may optionally be interrupted by at least one nitrogen-containing radical and optionally interrupted by at least one heteroatom chosen from an oxygen atom, a sulphur atom and a nitrogen atom, further wherein said divalent alkylene chains may optionally be terminated with at least one nitrogen-containing radical and optionally interrupted by at least one heteroatom chosen from an oxygen atom, a sulphur atom and a nitrogen atom, and further wherein said divalent alkylene chains may optionally be substituted with at least one radical chosen from hydroxyl radicals and $C_1$–$C_6$ alkoxy radicals;
- $R_9$ and $R_{10}$, which may be identical or different, are each chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals and linker arms Y;
- $R_{11}$, $R_{12}$, $R_{13}$, $R_{14}$, $R_{15}$ and $R_{16}$, which may be identical or different, are each chosen from a hydrogen atom, linker arms Y and $C_1$–$C_4$ alkyl radicals;
with the proviso that only one linker arm Y is present in each compound of formula (III).

16. A composition according to claim 15, wherein said double bases of formula (III) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylene-diamine, N,N'-bis(ethyl)-N,N'-bis(4'-amino-3'-methylphenyl) ethylenediamine, 1,8-bis(2,5-diaminophenoxy)-3,5-dioxaoctane and the acid addition salts of any of the foregoing.

17. A composition according to claim 16, wherein said double bases are chosen from N,N'-bis(β-hydroxyethyl)-N,N'-bis(4'-aminophenyl)-1,3-diaminopropanol, 1,8-bis(2,5-diaminophenoxy)-3,5-dioxaoctane and the acid addition salts of any of the foregoing.

18. A composition according to claim 9, wherein said para-aminophenols are chosen from compounds of formula (IV) and the acid addition salts thereof:

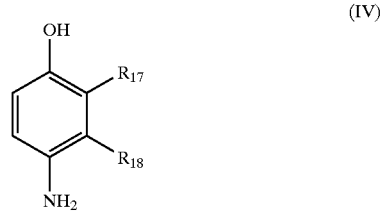

(IV)

wherein:
- $R_{17}$ is chosen from a hydrogen atom, halogen atoms, $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$ aminoalkyl radicals and hydroxy($C_1$–$C_4$)alkylamino ($C_1$–$C_4$)alkyl radicals; and
- $R_{18}$ is chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, cyano($C_1$–$C_4$)alkyl radicals and ($C_1$–$C_4$)alkoxy($C_1$–$C_4$)alkyl radicals,
with the proviso that at least one of $R_{17}$ and $R_{18}$ is a hydrogen atom.

19. A composition according to claim 18, wherein said para-aminophenols of formula (IV) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol and the acid addition salts of any of the foregoing.

20. A composition according to claim 9, wherein said ortho-aminophenols are chosen from 2-aminophenol, 2-amino-5-methylphenol, 2-amino-6-methylphenol, 5-acetamido-2-aminophenol and the acid addition salts of any of the foregoing.

21. A composition according to claim 9, wherein said heterocyclic bases are chosen from pyridine derivatives, pyrimidine derivatives, pyrazole derivatives and the acid addition salts of any of the foregoing.

22. A composition according to claim 1, wherein said at least one oxidation base is present in an amount ranging from 0.0005% to 12% by weight relative to the total weight of said composition.

23. A composition according to claim 19, wherein said at least one oxidation base is present in an amount ranging from 0.005% to 6% by weight relative to the total weight of said composition.

24. A composition according to claim 1, further comprising at least one additional coupler different from said indolizine derivatives of formula (I) and the acid addition salts thereof.

25. A composition according to claim 24, wherein said at least one additional coupler is chosen from meta-phenylenediamines, meta-aminophenols, meta-diphenols, heterocyclic couplers and the acid addition salts thereof.

26. A composition according to claim 25, wherein said heterocyclic couplers are chosen from indole derivatives, indoline derivatives, benzimidazole derivatives, benzomorpholine derivatives, sesamol derivatives, pyridine derivatives, pyrimidine derivatives, pyrazole derivatives and the acid addition salts thereof.

27. A composition according to claim 24, wherein said at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methyl-indole, 6-hydroxyindoline, 2,6-dihydroxy-4-methylpyridine, 1-H-3-methylpyrazol-5-one, 1-phenyl-3-methylpyrazol-5-one and the addition salts of any of the foregoing.

28. A composition according to claim 24, wherein said at least one additional coupler is present in an amount ranging from 0.0001% to 10% by weight relative to the total weight of said composition.

29. A composition according to claim 28, wherein said at least one additional coupler is present in an amount ranging from 0.005% to 5% by weight relative to the total weight of said composition.

30. A composition according to claim 1, further comprising at least one direct dye.

31. A composition according to claim 1, wherein said acid addition salts are chosen from hydrochlorides, hydrobromides, sulphates, tartrates, lactates and acetates.

32. A composition according to claim 1, wherein said medium suitable for dyeing is chosen from water and a mixture of water and at least one organic solvent.

33. A composition according to claim 32, wherein said at least one organic solvent is chosen from $C_1$–$C_4$ alkanols, glycerol, glycols, glycol ethers and aromatic alcohols.

34. A composition according to claim 32, wherein said at least one organic solvent is present in an amount ranging from 1% to 40% by weight relative to the total weight of said composition.

35. A composition according to claim 1, wherein said composition has a pH ranging from 3 to 12.

36. A composition according to claim 1, wherein said composition is in the form of a liquid, a cream or a gel.

37. A process for oxidation dyeing of keratin fibers comprising:
applying to said keratin fibers for a sufficient time to develop a desired color at least one dye composition comprising, in a medium suitable for dyeing, (i) at least one oxidation base and (ii) at least one coupler chosen from indolizine derivatives of formula (I) and the acid addition salts thereof:

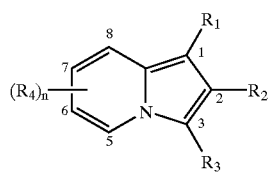

(I)

wherein:
n is an integer ranging from 0 to 4;
$R_1$ and $R_3$, which may be identical or different, are each chosen from a hydrogen atom; halogen atoms; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino($C_1$–$C_4$)alkyl radicals; ($C_1$–$C_4$)alkoxy($C_1$–$C_4$)alkyl radicals; mono($C_1$–$C_4$)alkylamino($C_1$–$C_4$)alkyl radicals; di($C_1$–$C_4$)alkylamino($C_1$–$C_4$)alkyl radicals; aminocarboxy ($C_1$–$C_4$)alkyl radicals; acetyl($C_1$–$C_4$)alkylamino ($C_1$–$C_4$)alkyl radicals; and aromatic rings, optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$) alkylamino($C_1$–$C_4$)alkyl radicals, carboxyl radicals and sulphoxy radicals;
wherein $R_3$ may optionally further be chosen from 5- and 6-membered unsaturated heterocycles; and
with the proviso that at least one of $R_1$ and $R_3$ is a hydrogen atom;
$R_2$ and $R_4$, which may be identical or different, are each chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono($C_1$–$C_4$)alkylamino ($C_1$–$C_4$)alkyl radicals, di($C_1$–$C_4$)alkylamino($C_1$–$C_4$) alkyl radicals, carboxyl radicals, cyano radicals, carboxy($C_1$–$C_4$)alkyl radicals, nitro radicals, and 5- and 6-membered aromatic rings, optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$) alkylamino($C_1$–$C_4$)alkyl radicals, carboxyl radicals and sulphoxy radicals.

38. A process according to claim 37, further comprising applying to said keratin fibers at least one oxidizing composition.

39. A process according to claim 37, wherein said at least one dye composition further comprises at least one oxidizing agent.

40. A process according to claim 37, wherein said desired color is developed at acidic, neutral or alkaline pH.

41. A process according to claim 39, wherein said at least one oxidizing agent is added to said at least one dye composition at the time of application.

42. A process according to claim 38, wherein said at least one oxidizing composition comprises at least one oxidizing agent.

43. A process according to claim 38, wherein said at least one oxidizing composition is applied to said keratin fibers simultaneously with said at least one dye composition.

44. A process according to claim 38, wherein said at least one oxidizing composition is applied to said keratin fibers sequentially with said at least one composition.

45. A process according to claim 38, wherein said at least one oxidizing composition is mixed with said at least one dye composition prior to said applying.

46. A process according to claim 37, wherein said keratin fibers are human keratin fibers.

47. A process accordingly to claim 46, wherein said human keratin fibers are hair.

48. A process according to claim 39, wherein said at least one oxidizing agent is chosen from hydrogen peroxide, urea peroxide, alkali metal bromates, persalts, peracids and enzymes.

49. A process according to claim 48, wherein said persalts are chosen from perborates and persulphates.

50. A process according to claim 48, wherein said enzymes are chosen from peroxidases, laccases, tyrosinases and oxidoreductases.

51. A process according to claim 50, wherein said oxidoreductases are chosen from pyranose oxidase, glucose oxidase, glycerol oxidase, lactate oxidase, pyruvate oxidase and uricase.

52. A process according to claim 42, wherein said at least one oxidizing agent is chosen from hydrogen peroxide, urea peroxide, alkali metal bromates, persalts, peracids and enzymes.

53. A process according to claim 52, wherein said persalts are chosen from perborates and persulphates.

54. A process according to claim 52, wherein said enzymes are chosen from peroxidases, laccases, tyrosinases and oxidoreductases.

55. A process according to claim 54, wherein said oxidoreductases are chosen from pyranose oxidase, glucose oxidase, glycerol oxidase, lactate oxidase, pyruvate oxidase and uricase.

56. A process according to claim 37, wherein said sufficient time to develop a desired color ranges from 3 minutes to 50 minutes.

57. A process according to claim 56, wherein said sufficient time to develop a desired color ranges from 5 minutes to 30 minutes.

58. A process according to claim 37, further comprising rinsing said keratin fibers.

59. A process according to claim 58, further comprising washing said keratin fibers with shampoo.

60. A process according to claim 59, further comprising rinsing and drying said keratin fibers.

61. A process according to claim 45, wherein the pH of said at least one oxidizing composition mixed with said at least one dye composition ranges from 3 to 12.

62. A process according to claim 61, wherein the pH of said at least one oxidizing composition mixed with said at least one dye composition ranges from 5 to 11.

63. A multicompartment device or kit for oxidation dyeing of keratin fibers comprising a first compartment containing a first composition comprising, in a medium suitable for dyeing, (i) at least one oxidation base and (ii) at least one coupler chosen from indolizine derivatives of formula (I) and the acid addition salts thereof:

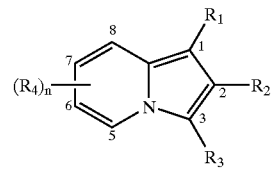

(I)

wherein:

n is an integer ranging from 0 to 4;

$R_1$ and $R_3$, which may be identical or different, are each chosen from a hydrogen atom; halogen atoms; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino($C_1$–$C_4$)alkyl radicals; ($C_1$–$C_4$)alkoxy($C_1$–$C_4$)alkyl radicals; mono($C_1$–$C_4$)alkylamino($C_1$–$C_4$)alkyl radicals; di($C_1$–$C_4$)alkylamino($C_1$–$C_4$)alkyl radicals; aminocarboxy($C_1$–$C_4$)alkyl radicals; acetyl($C_1$–$C_4$)alkylamino($C_1$–$C_4$)alkyl radicals; and aromatic rings, optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals;

wherein $R_3$ may optionally further be chosen from 5- and 6-membered unsaturated heterocycles; and with the proviso that at least one of $R_1$ and $R_3$ is a hydrogen atom;

$R_2$ and $R_4$, which may be identical or different, are each chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono($C_1$–$C_4$)alkylamino($C_1$–$C_4$)alkyl radicals, di($C_1$–$C_4$)alkylamino($C_1$–$C_4$)alkyl radicals, carboxyl radicals, cyano radicals, carboxy($C_1$–$C_4$)alkyl radicals, nitro radicals, and 5- and 6-membered aromatic rings, optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals; and a second compartment containing a second composition comprising at least one oxidizing composition.

* * * * *

UNITED STATES PATENT AND TRADEMARK OFFICE
CERTIFICATE OF CORRECTION

PATENT NO. : 6,572,664 B2
DATED : June 3, 2003
INVENTOR(S) : Philippe Breton et al.

It is certified that error appears in the above-identified patent and that said Letters Patent is hereby corrected as shown below:

Column 17,
Line 45, delete "6-carboxy-2-phenylindolizine;".

Column 18,
Line 35, "and a fluorine" should read -- and fluorine --.

Column 19,
Line 58, "tetramethylene-diamine," should read -- tetramethylenediamine, --.

Column 20,
Line 63, "hetereocyclic" should read -- heterocyclic --.

Column 22,
Line 66, "accordingly" should read -- according --.

Signed and Sealed this

Twenty-fifth Day of November, 2003

JAMES E. ROGAN
*Director of the United States Patent and Trademark Office*